United States Patent
Sturm et al.

(10) Patent No.: US 9,630,895 B2
(45) Date of Patent: Apr. 25, 2017

(54) STORAGE AND STABILIZATION OF ACETYLENE

(71) Applicant: ADVANCED TECHNOLOGY MATERIALS, INC., Danbury, CT (US)

(72) Inventors: Edward A. Sturm, New Milford, CT (US); Thomas H. Baum, New Fairfield, CT (US); J. Donald Carruthers, Fairfield, CT (US)

(73) Assignee: Entegris, Inc., Billerica, MA (US)

( * ) Notice: Subject to any disclaimer, the term of this patent is extended or adjusted under 35 U.S.C. 154(b) by 340 days.

(21) Appl. No.: 14/390,784

(22) PCT Filed: Apr. 13, 2013

(86) PCT No.: PCT/US2013/036504
§ 371 (c)(1),
(2) Date: Oct. 5, 2014

(87) PCT Pub. No.: WO2013/155499
PCT Pub. Date: Oct. 17, 2013

(65) Prior Publication Data
US 2015/0119610 A1 Apr. 30, 2015

Related U.S. Application Data

(60) Provisional application No. 61/623,727, filed on Apr. 13, 2012.

(51) Int. Cl.
*B01D 53/04* (2006.01)
*F17C 11/00* (2006.01)
(Continued)

(52) U.S. Cl.
CPC ............... *C07C 7/20* (2013.01); *B01D 53/02* (2013.01); *B01J 20/20* (2013.01); *B01J 20/2808* (2013.01);
(Continued)

(58) Field of Classification Search
CPC .. B01D 53/02; B01D 53/04; B01D 2253/102; B01D 2253/304; B01D 2253/306;
(Continued)

(56) References Cited

U.S. PATENT DOCUMENTS 3,773,168 A 11/1973 Meinass
4,046,709 A 9/1977 Yuki
(Continued)

FOREIGN PATENT DOCUMENTS

CN 101405069 A 4/2009
EP 1064996 A1 1/2001
(Continued)

OTHER PUBLICATIONS

Xie, "6 Preparation and Characterization of Vinylidene Chloride Polymer-based Porous Carbon", Zhejiang University Master's Thesis: Preparation of Vinylidene Chloride Polymer and Vinylidene Chloride Polymer-based Porous Carbon, Apr. 20, 2009, pp. 43-58.
(Continued)

*Primary Examiner* — Frank Lawrence
(74) *Attorney, Agent, or Firm* — Entergis, Inc. Legal Dept.; Nidhi G. Kissoon; John E. Pillion

(57) ABSTRACT

A carbon adsorbent adapted for adsorptive storage and subsequent desorptive release of a decomposition-susceptible gas is described. Such carbon adsorbent comprises porosity in which mesopore volume is less than 0.25 cm$^3$/gm of carbon adsorbent, in which the porosity comprises at least 80% by volume micropores, and at least 65% by volume of the micropores have pore diameter in a range of from 0.3 to
(Continued)

0.72 nm. The carbon adsorbent has a nitrogen adsorption BET surface area greater than 800 m²/g of carbon adsorbent, measured at 77° K, and a bulk density that is greater than 0.55 g/cc of carbon adsorbent. The carbon adsorbent can be utilized in gas storage and dispensing packages of varying type, to provide a safe and reliable source of decomposition-susceptible gas, e.g., acetylene for applications such as gas welding/cutting applications, atomic absorption spectroscopy applications, chemical synthesis and microelectronic products manufacturing.

21 Claims, 3 Drawing Sheets

(51) Int. Cl.
| C07C 7/20 | (2006.01) |
| B01D 53/02 | (2006.01) |
| C01B 31/10 | (2006.01) |
| B01J 20/20 | (2006.01) |
| B01J 20/28 | (2006.01) |
| C01B 31/08 | (2006.01) |
| C07C 11/24 | (2006.01) |
| F17C 13/12 | (2006.01) |
| B01J 20/30 | (2006.01) |

(52) U.S. Cl.
CPC ... *B01J 20/28011* (2013.01); *B01J 20/28057* (2013.01); *B01J 20/3078* (2013.01); *C01B 31/08* (2013.01); *C01B 31/083* (2013.01); *C01B 31/10* (2013.01); *C07C 11/24* (2013.01); *F17C 11/002* (2013.01); *F17C 13/123* (2013.01); *B01D 2253/102* (2013.01); *B01D 2253/304* (2013.01); *B01D 2253/306* (2013.01); *B01D 2253/31* (2013.01); *B01D 2257/702* (2013.01); *B01D 2259/4525* (2013.01)

(58) Field of Classification Search
CPC .......... B01D 2253/31; B01D 2257/702; B01D 2259/4525; B01J 20/20; B01J 20/28011; B01J 20/28057; B01J 20/2808; B01J 20/3078; C01B 31/08; C01B 31/083; C01B 31/10; C07C 11/24; C07C 7/20; F17C 11/002; F17C 11/007; F17C 13/123
USPC .............. 96/108; 95/90, 116, 141, 143, 145; 55/DIG. 20; 502/416, 418, 437; 206/0.7
See application file for complete search history.

(56) References Cited

U.S. PATENT DOCUMENTS

| 5,614,459 | A | 3/1997 | Mondragon et al. | |
| 5,993,766 | A | 11/1999 | Tom et al. | |
| 6,006,797 | A | 12/1999 | Buelow et al. | |
| 6,743,278 | B1 | 6/2004 | Carruthers | |
| 2002/0020292 | A1* | 2/2002 | Wojtowicz | B01D 53/02 95/116 |
| 2005/0188846 | A1 | 9/2005 | Carruthers | |
| 2008/0207442 | A1* | 8/2008 | Pfeifer | B01J 20/20 502/416 |
| 2009/0188392 | A1 | 7/2009 | Carruthers | |
| 2009/0317613 | A1* | 12/2009 | Meisner | B01J 20/20 428/219 |
| 2010/0125039 | A1* | 5/2010 | Banerjee | C01B 31/083 502/417 |
| 2011/0005392 | A1 | 1/2011 | Pirngruber et al. | |
| 2011/0127174 | A1 | 6/2011 | Heinrich et al. | |
| 2012/0024157 | A1 | 2/2012 | Maheshwary et al. | |
| 2012/0174936 | A1* | 7/2012 | Branton | A24D 3/163 131/331 |

FOREIGN PATENT DOCUMENTS

| WO | 0224310 | A1 | 3/2002 |
| WO | 02068324 | A1 | 9/2002 |
| WO | 2007090104 | A2 | 8/2007 |
| WO | 2008058231 | A2 | 5/2008 |
| WO | 2009011750 | A2 | 1/2009 |
| WO | 2012106218 | A2 | 8/2012 |

OTHER PUBLICATIONS

Xie, "6 Preparation and Characterization of Vinylidene Chloride Polymer-based Porous Carbon", Zhejiang University Master's Thesis: Preparation of Vinylidene Chloride Polymer and Vinylidene Chloride Polymer-based Porous Carbon, Apr. 20, 2009, pp. 43-58 (English Translation).

Jimenez-Cruz, F., et al., "Adsorption of n-Heptane and 2-Methylheptane in the Gas Phase on Polyvinylidene Chloride-Based Microporous Activated Carbon", "Energy and Fuels", Aug. 17, 2007, pp. 2929-2934, vol. 21.

Jung, H., et al., "Pore Structure Characterization of Poly(vinylidene chloride)-Derived Nanoporous Carbons", "Carbon Letters", Oct. 31, 2012, pp. 236-242, vol. 13, No. 4.

Xu, B., et al., "An Activation-Free Method for Preparing Microporous Carbon by the Pyrolysis of Poly(Vinylidene Fluoride)", "Carbon", Apr. 14, 2010, pp. 2812-2814, vol. 48.

Notification of Reasons for Refusal from JP application 2015-505969, mailed Nov. 15, 2016, 8 pages.

* cited by examiner

STORAGE AND STABILIZATION OF ACETYLENE

CROSS-REFERENCE TO RELATED APPLICATION APPLICATIONS

This application is a U.S. national phase under the provisions of 35 U.S.C. §371 of International Patent Application No. PCT/US13/36504 filed Apr. 13, 2013, which in turn claims priority of U.S. Provisional Patent Application No. 61/623,727 filed Apr. 13, 2012. The disclosures of such international patent application and U.S. priority patent application are hereby incorporated herein by reference, in their respective entireties, for all purposes.

FIELD

The present invention relates to adsorbent-based storage and dispensing of decomposition-susceptible gas such as acetylene, and to adsorbents, supply packages, and methods therefor.

DESCRIPTION OF THE RELATED ART

Acetylene is used industrially in a variety of applications, including usage as a fuel gas for gas welding/cutting applications, in atomic absorption spectroscopy applications, and as a source gas for chemical synthesis and microelectronic products manufacturing. Acetylene has the disadvantage of being very unstable due to its high chemical reactivity. Pure acetylene is known to spontaneously react explosively at pressures above 2 bar (29 psig, 1500 Torr, 200 kilopascals).

The unstable character of acetylene, in addition to entailing the risk of severe explosive hazard, also imparts susceptibility to polymerization and formation of poly(acetylenes) and/or highly reactive metallated species in the presence of metals.

In addition, acetylene is often accompanied by impurities such as methane, ethane, propane, carbon monoxide and other assorted organic species.

As a result of its unstable character and extreme reactivity, acetylene cannot be stored in a homogeneous gas phase in pressurized gas supply vessels, such as are conventionally utilized for the storage, transport and delivery of a wide variety of other industrial gases.

The art therefore has typically supplied acetylene in a dissolved form, wherein the acetylene gas has been solubilized in a suitable solvent, such as acetone, to reduce its activity to commercially acceptable levels. Acetone dissolves 25 times its own volume of acetylene for each atmosphere of pressure at a temperature 15° C. A typical commercial package for acetylene storage and dispensing includes a metal vessel containing a solid porous mass in which acetone or other solvent is contained, and in which acetylene is dissolved. When acetone is employed, it will absorb acetylene in a volume of about 10 times the volume of the metal vessel for every atmosphere of pressure to which the gases subjected. This packaging of acetylene greatly minimizes the danger of explosion, and has a limiting safety pressure level of 271 psia (1868.5 kPa) at 15° C.

The primary disadvantages of such conventional packaging of acetylene gas are its inability to provide acetylene at high flow rates, particularly when the metal vessel is in a near-empty condition, and the fact that acetone is present and invariably contaminates the dispensed acetylene gas. In applications such as chemical synthesis and microelectronics manufacturing, such acetone contamination may be highly disadvantageous. Additional disadvantages of conventional solvent-based storage and dispensing acetylene packages include limited storage capacity due to constraints on maximum permissible pressure, and rapid decrease in dispensed acetylene pressure with decreasing ambient temperature.

U.S. Pat. No. 6,006,797 to Martin Bülow, et al. discloses storage of acetylene at elevated pressure on a carbonaceous adsorbent on which acetylene is reversibly absorbable. The adsorbent disclosed in such patent has a micropore volume (pore diameter <2 nm) of at least 0.5 $cm^3$ per gram, a mesopore volume (pore diameter of 2-50 nanometers) of at least 0.5 $cm^3$ per gram, a bulk density of at least 0.25 g per cubic centimeter, and a surface area per unit volume of at least 400 $m^2$ per cubic centimeter. Alternatively or in addition to the micropore volume and mesopore volume restrictions, the specific volume of pores having a diameter in a range of 1.5 to 3.0 nm is at least 0.3 $cm^3$ per gram, but some of the specific mesopore volume and the specific micropore volume should always be at least 1.0 $cm^3$ per gram. The Bülow, et al. patent provides that at least 75% of the specific mesopore volume is contributed by mesopores having a diameter in a range of from 2 to 5 nanometers and at least 90% of the micropores have a diameter of at least 0.4 nm. The adsorbent may be in a particulate or monolithic form.

The Bülow, et al. patent identifies pores having a diameter in a range of from 1.5 to 3.0 nm as being particularly effective in absorbing acetylene, and the patent states that it is generally preferable to maximize the "density" of such pores or their specific mesopore volume, with pore sizes in the range of from 1.8 to 2.5 nm believed to be most effective.

While the mesoporous adsorbent materials of the Bülow, et al. patent are stated to be efficacious for storage and dispensing of acetylene, the presence of mesopores and micropores each having a volume of at least 0.5 $cm^3$ per gram has the effect that the pores of different sizes in the respective mesopore and micropore regimes will behave differently as regards their adsorption and desorption performance, and the effect of temperature/pressure variability may substantially alter the amount of acetylene that can be stored and subsequently desorbed, as well as substantially altering the rate at which acetylene is able to be dispensed from the vessel in which such mesopore/micropore carbonaceous adsorbent is employed.

In consequence, the art continues to seek improvements in storage and dispensing systems for acetylene and other decomposition-susceptible gases.

SUMMARY

The present disclosure relates to storage and dispensing of decomposition-susceptible gases such as acetylene, and more specifically to carbon adsorbent having utility for sorptively storing and desorptively dispensing such gases, to gas storage and dispensing vessels comprising such carbon adsorbent, and to methods of supplying decomposition-susceptible gases such as acetylene, e.g., for fuel, spectroscopy, microelectronics manufacturing, or chemical synthesis applications.

In one aspect, the disclosure relates to a carbon adsorbent adapted for adsorptive storage and subsequent desorptive release of the decomposition-susceptible gas, such carbon adsorbent comprising porosity in which mesopore volume is less than 0.25 $cm^3/gm$ of carbon adsorbent, in which the porosity comprises at least 80% by volume micropores, and at least 65% by volume of the micropores have pore diameter in a range of from 0.3 to 0.72 nm, wherein the carbon adsorbent has a nitrogen adsorption BET surface area greater than 800 m2/g of carbon adsorbent, as measured at 77° K, and a bulk density that is greater than 0.55 g/cc of carbon adsorbent.

In another aspect, the disclosure relates to a carbon adsorbent of the disclosure, having acetylene or other decomposition-susceptible gas adsorbed thereon.

In a further aspect, the disclosure relates to a gas storage and dispensing package for such decomposition-susceptible gas, comprising a gas storage and dispensing vessel comprising an interior volume, and carbon adsorbent of the disclosure disposed in said interior volume.

A further aspect of the disclosure relates to a method of packaging the decomposition-susceptible gas, e.g., acetylene, for use in supplying same at a point of use, such method comprising adsorbing the decomposition-susceptible gas on a carbon adsorbent of the disclosure, to enable the decomposition-susceptible gas to be provided in absorbed form on such carbon adsorbent at the point of use, for desorption at such point of use.

A still further aspect of the disclosure relates to a method of fabricating a package for use in supply of a decomposition-susceptible gas, such as acetylene gas, to a point of use thereof, such method comprising fabricating a storage and dispensing vessel and disposing therein a carbon adsorbent of the disclosure.

Yet another aspect the disclosure relates to a method of supplying a decomposition-susceptible gas such as acetylene at a point of use, such method comprising providing at the point of use a carbon adsorbent according to the present disclosure, having the decomposition-susceptible gas adsorbed thereon, and desorbing such decomposition-susceptible gas from the carbon adsorbent at the point of use.

Other aspects, features and embodiments of the disclosure will be more fully apparent from the ensuing description and appended claims.

DETAILED DESCRIPTION

Figure 1:
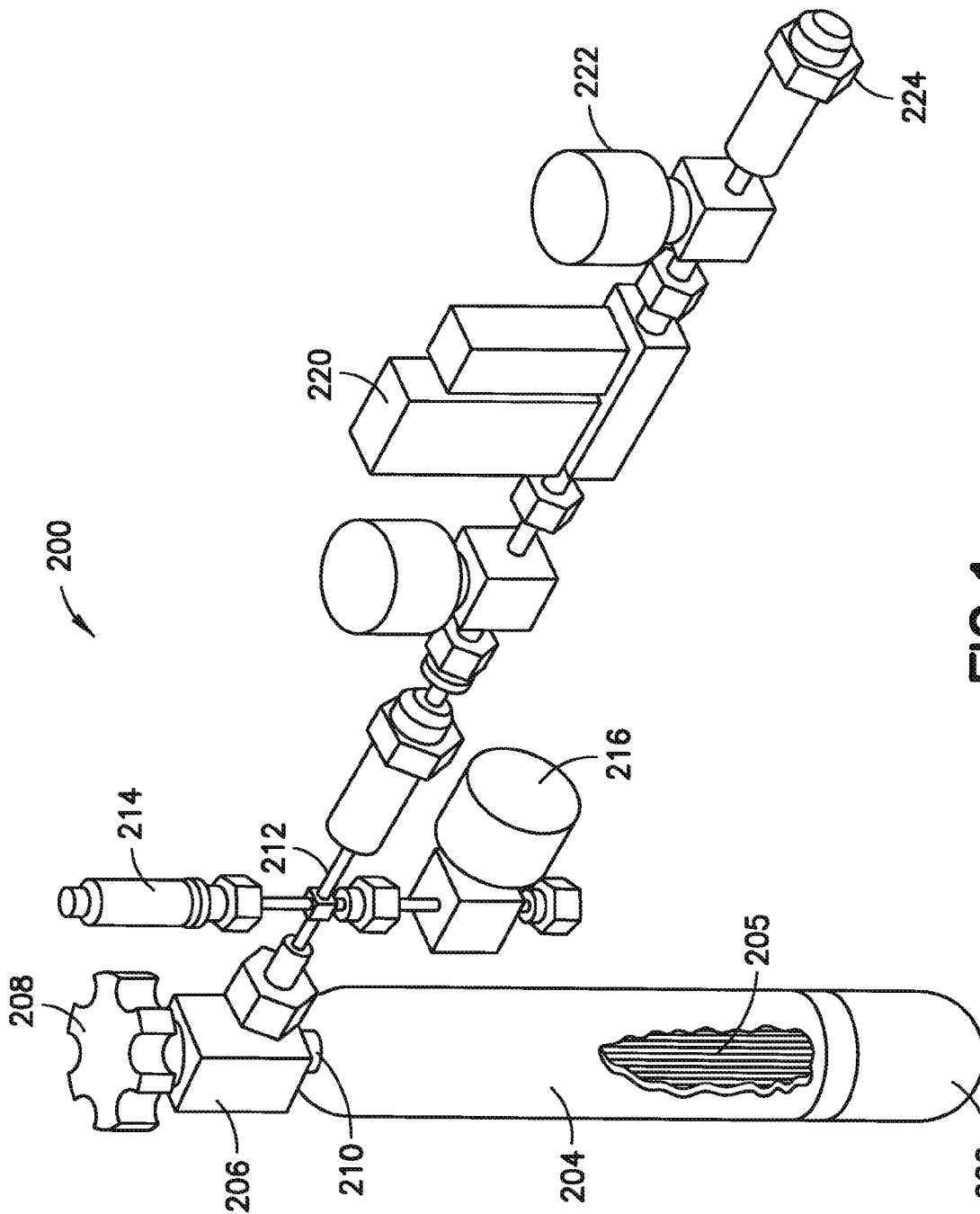
FIG. 1 is a schematic representation of a storage and delivery system utilizing a carbon monolithic sorbent, according to one embodiment of the present disclosure.

The present invention relates to carbon adsorbent having utility for storage and dispensing of decomposition-susceptible gases, e.g., acetylene, to gas storage and dispensing packages utilizing such adsorbent, and to methods utilizing such carbon adsorbent and dispensing packages for supply of decomposition-susceptible gas.

Although the description herein is primarily directed to acetylene stabilization, it will be recognized that the utility of the disclosure is not thus limited, but rather extends to and encompasses the stabilization of other reactive and sensitive gases by the adsorbent approach to gas storage, transport and delivery described herein. Such approach therefore may be employed with reactive and sensitive gases including, without limitation: formaldehyde; acetylene compounds of the formula $R^1$—C≡C—$R^2$ in which each of $R^1$ and $R^2$ is independently selected from H, $C_1$-$C_{12}$ alkyl, $C_6$-$C_{10}$ aryl, $C_6$-$C_{12}$ cycloalkyl, amino, alkylamino, dialkylamino, alkylaryl wherein alkyl is $C_1$-$C_{12}$ alkyl and aryl is $C_6$-$C_{10}$ aryl, arylalkyl wherein alkyl is $C_1$-$C_{12}$ alkyl and aryl is $C_6$-$C_{10}$ aryl, silyl, and $R^3{}_3$Si— wherein each $R^3$ is independently selected from H and $C_1$-$C_{12}$ alkyl; other non-saturated straight chain hydrocarbons; methylene; ethylene; diborane; boranes; germane; fluorogermanes; carboranes; alanes; aluminium hydrides; silane; chlorosilanes; digallane; chlorogallanes; and stannane.

As used herein and in the appended claims, the singular forms "a", "and", and "the" include plural referents unless the context clearly dictates otherwise.

"Alkyls" as used herein include, but are not limited to, methyl, ethyl, propyl, butyl, pentyl, hexyl, heptyl, octyl, nonyl, decyl, undecyl and dodecyl, including straight chain as well as branched groups of such types.

"Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like.

"Cycloalkyls" as used herein include, but are not limited to cyclopropyl, cyclobutyl, cyclopentyl, cyclohexyl and the like.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the disclosure, and that ranges of carbon numbers specifically excluding a carbon number or numbers are included in the disclosure, and sub-ranges excluding either or both of carbon number limits of specified ranges are also included in the disclosure. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the disclosure, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

The reactive and sensitive gas species of the disclosure may be further specified in specific embodiments by provisos or limitations excluding specific substituents, groups, moieties or structures, in relation to various specifications and exemplifications thereof set forth herein. Thus, the disclosure contemplates restrictively defined compositions, e.g., a gas composition wherein $R^1$ is $C_1$-$C_{12}$ alkyl, with the proviso that $R^1 \neq C_4$ alkyl when $R^2$ is silyl.

The present disclosure is based on the discovery that carbon adsorbents having mesopore volume substantially less than 0.25 cubic centimeters of mesopore volume per gram, are nonetheless highly useful for storage and dispensing of acetylene gas and other decomposition-susceptible gases, and afford substantial advantages over the prior art. These substantial advantages include, for example, a more uniform and predictable adsorption/desorption performance, less susceptibility to variations in adsorbent performance as a result of temperature/pressure effects, more uniform dispensing rate, and greater storage capacities than those described in the prior art.

In addition to having mesopore volume that is less than 0.25 cm$^3$ per gram of adsorbent, the carbon adsorbent of the present disclosure has the following characteristics: (i) at least 80% of its porosity provided by micropores (pore diameter <2 nm), and with at least 65% of such microporosity comprising pores having diameter in a range of from about 0.3 to about 0.72 nanometer; (ii) a nitrogen adsorption BET surface area greater than 800 m$^2$/g, as measured at 77° K; and (iii) a bulk density that is greater than 0.55 g/cc, e.g., a bulk density in a range of from about 0.6 g/cc to about 1.6 g/cc.

Bulk density values set out herein in reference to the carbon adsorbents of the present disclosure are to be understood as being measured by mensuration or the procedure of the American Society of Testing and Materials (ASTM), in particular, ASTM 4164.

The disclosure contemplates a carbon adsorbent adapted for adsorptive storage and subsequent desorptive release of acetylene or other decomposition-susceptible gas. Such carbon adsorbent comprises porosity in which (i) mesopore volume is less than 0.25 cm$^3$/gm of carbon adsorbent, e.g., in a range of from 0 to 0.24 cm$^3$/gm, (ii) in which the porosity comprises at least 80% by volume micropores, e.g., in a range of from 80% to 100%, (iii) at least 65% by volume of the micropores have pore diameter in a range of from 0.3 to 0.72 nm, e.g., in a range of from 65% to 100%. Such carbon adsorbent also has a nitrogen adsorption BET surface area greater than 800 m$^2$/g of carbon adsorbent, as measured at 77° K, e.g., in a range of from 810 to 3500 m$^2$/g, and a bulk density that is greater than 0.55 g/cc of carbon adsorbent, e.g., in a range of from 0.6 to 2.5 g/cc.

In various embodiments, such carbon adsorbent may have one or more of the following characteristics, as compatible with one another in specific embodiments: bulk density in a range of from 0.55 g/cc to 1.6 g/cc; nitrogen adsorption BET surface area greater than 1000 m$^2$/g, preferably greater than 1200 m$^2$/g, and most preferably greater than 1400 m$^2$/g, all as measured at 77° K; particulate form, comprising particles of a diameter or major dimension in a range of from 0.3 to 4 mm; particulate form, comprising particles with a piece density that is greater than 0.8 g/cc carbon adsorbent, e.g., a piece density of from 0.85 to 4 g/cc; monolithic form, e.g., in the form of a brick, block, ingot, or disk article; bulk density of from 0.80 to 1.6 g/cc of carbon adsorbent; three-dimensional (x, y, z) character wherein each of such dimensions is greater than 1.5 cm, and preferably greater than 2 cm; formation as a pyrolyzate of a material selected from the group consisting of polyvinylidene chloride, phenol-formaldehyde resins, polyfurfuryl alcohol, polyvinylidene fluoride, coconut shells, peanut shells, peach pits, olive stones, polyacrylonitrile, and polyacrylamide; fill density measured for acetylene gas at 25° C. and pressure of 650 Torr (86.7 kPa), of greater than 100 gm acetylene/liter of carbon adsorbent, more preferably greater than 120 g acetylene/liter of carbon adsorbent, and most preferably greater than 140 g acetylene/liter of carbon adsorbent, e.g., a fill density of from 110 to 250 g acetylene/liter of carbon adsorbent.

The disclosure contemplates carbon adsorbents of varied types within the foregoing description, as decomposition-susceptible gas storage media having decomposition-susceptible gas adsorbed thereon, e.g., acetylene or an acetylene derivative.

The disclosure further contemplates a gas storage and dispensing package for a decomposition-susceptible gas, comprising a gas storage and dispensing vessel comprising an interior volume, and carbon adsorbent of the disclosure disposed in the interior volume having reversible adsorptive affinity for the decomposition-susceptible gas. Such gas storage and dispensing package in specific embodiments further comprises a valve head assembly including a valve that is closable to contain the decomposition-susceptible gas in the gas storage and dispensing vessel, and openable to enable dispensing of gas from the gas storage and dispensing vessel.

The decomposition-susceptible gas storage and dispensing package in various embodiments further comprises a deflagration suppression component or assembly that is configured to suppress deflagration of the decomposition-susceptible gas deriving from the gas storage and dispensing vessel, or in which the carbon adsorbent is treated to suppress the potential for deflagration.

In general, the carbon adsorbent may be treated to enhance its deflagration-resistance, by any treatment that is effective to passivate or deactivate the adsorbent surface such that the interaction of the gas molecules with the surface is restricted to physical adsorption without chemical reaction.

For example, the carbon adsorbent may be treated by chemical treatment to remove Lewis acid sites of the adsorbent. Additionally, or alternatively, the carbon adsorbent may be treated by surface neutralization treatments of various suitable types.

In various embodiments, the carbon adsorbent is treated to render it deflagration-resistant in character by a process comprising: (a) cyclically purging the carbon adsorbent with an inert gas; (b) heating the carbon adsorbent under vacuum to elevated temperature; (c) subsequently cyclically purging the carbon adsorbent with an inert gas; (d) contacting the carbon adsorbent with a low concentration of the intended storage gas at elevated temperature; (e) removing the gas; and (f) cooling the carbon adsorbent under vacuum to ambient temperature.

In other embodiments, the carbon adsorbent is treated to render it deflagration-resistant in character by a process comprising: (a) cyclically purging the carbon adsorbent with an inert gas; (b) heating the carbon adsorbent under vacuum to elevated temperature; (c) cooling the carbon adsorbent under vacuum to ambient temperature; (d) gradually contacting the carbon adsorbent with a low concentration of the intended storage gas; (e) warming the vessel containing the gas to a temperature in a range of from 35° C. to 180° C.; (f) allowing the vessel pressure to stabilize; (g) evacuating and cycle purging the carbon adsorbent; and (h) cooling the carbon adsorbent under vacuum to ambient temperature.

The gas supply package of the present disclosure may be of any suitable size. In various embodiments, the gas storage and dispensing vessel in the gas supply package may have an interior volume that is in a range of from 1 to 25 liters, or in a range of from 25 to 200 liters, or in other specific size range, wherein the interior volume is measured as empty volume, without adsorbent or decomposition-susceptible gas therein.

In the foregoing treatments for enhancing deflagration-resistance, the low concentration of the intended storage gas may be a concentration of from 5% to 40% by volume, based on total volume of the storage gas and accompanying diluent gas.

Gas storage and dispensing packages of the disclosure may be integrated with a transport vehicle, e.g., mounted on a motive transport vehicle or constituting a structural portion thereof, e.g., wherein the gas storage and dispensing vessel comprises a tube trailer vessel.

Gas storage and dispensing packages of the disclosure may contain any suitable amount of decomposition-susceptible gas, consistent with the sorptive capacity of the specific carbon adsorbent disposed in the interior volume of the acetylene storage and dispensing vessel. The gas storage and dispensing package may be coupled and dispensing relationship to a gas-utilizing process tool, e.g., a microelectronic product manufacturing tool, or other process apparatus in which the dispensed gas is utilized.

The disclosure further contemplates a method of packaging decomposition-susceptible gas for use in supplying same at a point of use, such method comprising adsorbing decomposition-susceptible gas on a carbon adsorbent of the present disclosure, to enable the gas to be provided in absorbed form on the carbon adsorbent at the point of use, for desorption at such point of use. In such method, the carbon adsorbent can be provided in a gas storage and dispensing vessel, to which the decomposition-susceptible gas is charged for the aforementioned adsorbing.

Also contemplated by the disclosure is a method of fabricating a package for use in supply of the decomposition-susceptible gas to a point of use thereof, such method comprising fabricating a gas storage and dispensing vessel and disposing therein a carbon adsorbent of the disclosure.

The disclosure also contemplates a method of supplying a decomposition-susceptible gas, e.g., acetylene, at a point of use, such method comprising providing at the point of use a carbon adsorbent of the disclosure, having the decomposition-susceptible gas adsorbed thereon, and desorbing the decomposition-susceptible gas from the carbon adsorbent at the point of use.

Consistent with the foregoing discussion, the carbon adsorbent in accordance with the present disclosure may be provided in any suitable size, shape and form. As discussed, the carbon adsorbent can be particulate in character, comprising particles in a size (diameter or major dimension) range of from 0.3 to 4 mm, with a piece density that is greater than 0.8 g/cc. Alternatively, the carbon adsorbent may be in a monolithic form. Carbon monoliths useful in the broad practice of the present disclosure include gross brick, block and ingot forms, as bulk forms, preferably having three-dimensional (x, y, z) character wherein each of such dimensions is greater than 1.5, and preferably greater than 2 centimeters.

In one embodiment, the carbon adsorbent is provided as a carbon pyrolyzate monolith, in the form of disk-shaped articles of a same diameter, enabling such articles to be stacked in a vertical stack in an acetylene storage and dispensing vessel. In another embodiment, the carbon adsorbent is provided as a carbon pyrolyzate monolith of unitary character that is formed in situ in the gas storage and dispensing vessel, from a precursor resin introduced into the vessel and pyrolyzed therein to form the pyrolyzed carbon monolith, subsequent to which the vessel may be finished in the manufacturing of the corresponding gas storage and dispensing package, and thereafter charged with the decomposition-susceptible gas for adsorption thereof on the pyrolyzed carbon monolith.

In still another embodiment, the carbon monolith may be in the form of a monolith briquette, having a high bulk density (measured with voids), e.g., on the order of from about 0.80 to about 1.6 grams per cubic centimeter, preferably from 0.9 to 1.6 grams per cubic centimeter, more preferably from 1 to 1.3 grams per cubic centimeter, and most preferably from 1.05 to 1.25 grams per cubic centimeter, with high working capacity (high microporosity and low heel) and pore tortuosity that is sufficiently low to ensure ready and rapid rate adsorption and desorption.

Carbon adsorbent in accordance with the present disclosure can be formed from a suitable polymeric or other material, e.g., a material selected from among polyvinylidene chloride, phenol-formaldehyde resins, polyfurfuryl alcohol, polyvinylidene fluoride, coconut shells, peanut shells, peach pits, olive stones, polyacrylonitrile, polyacrylamide, etc., that is pressure-moldable, e.g., at a molding pressure up to about 20,000 psi or higher, to yield a pressure-molded "green resin" body that is pyrolyzable at temperature below 1000° C., preferably not exceeding about 900° C., e.g., in a range of from about 500° C. to about 900° C., and more preferably in a range of from about 600° C. to about 900° C., to yield a monolithic carbon material having a fill density of suitably high value for the intended decomposition-susceptible gas storage and dispensing application. Monolithic carbon sorbents useful in the practice of the present invention include those having a fill density measured for acetylene gas at 25° C. and a pressure of 650 torr that is in excess of 100 grams acetylene per liter of carbon adsorbent, preferably greater than 120 grams acetylene per liter of carbon adsorbent, and most preferably greater than 140 g acetylene per liter of carbon adsorbent.

The carbon adsorbent of the present disclosure is suitably manufactured as a pyrolysis product whose time, temperature and pressure conditions may be selectively varied to provide carbon adsorbent of the desired specific character for use as a gas storage and dispensing medium. The pyrolysis product can be activated by any suitable processing steps for enhancing the sorptive affinity of the material for the decomposition-susceptible gas or otherwise improving the characteristics of the adsorbent for use in gas storage and dispensing service.

For example, the activation process can include heating in a non-oxidizing atmosphere, e.g., of nitrogen, argon, helium or other non-oxidizing gas, followed by switching of the atmosphere to an oxidizing atmosphere, such as carbon dioxide or steam for a brief duration, before switching to a non-oxidizing atmosphere and cooling to ambient temperature (e.g., room temperature). The specifics of the activation process, e.g., the temperature levels and duration of the successive steps can be readily determined within the skill of the art, based on the disclosure herein, by simple variation of respective process conditions and analytic determination of the resulting adsorbent performance, such as acetylene fill density, porosimetry characterization, etc.

The activation process may be carried out prior to loading the carbon adsorbent in the gas storage and dispensing vessel, or alternatively, in some embodiments, the carbon adsorbent can be loaded into the gas storage and dispensing vessel, and the activation process conducted in situ, so that the gas storage and dispensing package is completed except for charging with the decomposition-susceptible gas, and such charging may be carried out at the manufacturing location for the package, or the storage and dispensing package may be fabricated and sent from the manufacturing location to a gas charging plant or facility, to introduce the decomposition-susceptible gas to the storage and dispensing vessel.

The decomposition-susceptible gas storage and dispensing package can in various embodiments further include a flame arrestor, "snuffer", or other deflagration suppression components and assemblies, to further augment the inherent safety of the storage and dispensing package. As previously mentioned, the carbon adsorbent may be treated to passivate or deactivate the surface so as to limit interaction of the adsorbent surface with the decomposition-susceptible gas to physical adsorption, without the occurrence of chemical reaction.

It will be recognized that the size, shape and materials of construction of the gas storage and dispensing vessel can be widely varied in the practice of the present disclosure. For example, the gas storage and dispensing vessel can be of a relatively small size and manually transportable character, e.g., having an interior volume in a range of from 1-25 liters (measured as empty volume), or vessels can be employed of intermediate volume, e.g., from 25 to 200 liters (measured as empty volume), or such vessels can be of any suitable large volume size, for the intended application and supply requirements at the locus of use of the supplied gas.

In various embodiments, the carbon adsorbents of the present disclosure may be utilized in transportable vessels of substantial size, e.g., sizes that are consistent with mechanized or motorized vehicles that are utilized to transport the vessels. For example, the adsorbents in some embodiments may be employed in tube trailer vessels, e.g., for transport by rail or by tractor-trailer arrangements. In one illustrative embodiment of such type, acetylene transport tubes are provided, having a diameter of 1 foot (0.3 m) and a length of 40 feet (12.2 m), providing a volume of about 31.4 cubic feet (890 liters). Each of such transport tubes will contain at least about 1100 pounds (500 kg) of carbon, hold about 180 kg of acetylene and provide 110 kg of usable capacity of acetylene.

Referring now to the drawings, FIG. 1 is a schematic representation of an acetylene storage and delivery package 200 utilizing a carbon monolithic sorbent, according to one embodiment of the present disclosure.

As shown, the storage and dispensing package 200 comprises a storage and dispensing vessel 204 that is joined at its upper portion to a valve head 206 comprising part of a dispensing assembly including manual actuator 208 for the valve head on the cylinder. In lieu of such manual actuator, an automatic valve actuator could be employed, such as a pneumatic valve actuator or actuator of other suitable type.

The vessel 204 can be formed of any suitable material of construction, e.g., comprising material such as metals, glasses, ceramics, vitreous materials, polymers, and composite materials. Illustrative metals for such purpose include steel, stainless steel, aluminum, copper, brass, bronze, and alloys thereof. The valve head is joined by means of coupling 210 to a dispensing conduit 212 having disposed therein a pressure transducer 214, an inert purge unit 216 for purging the dispensing assembly with inert gas, a mass flow controller 220 for maintaining constant flow rate through the dispensing conduit 212 during the dispensing operation, and a filter 222 for removing particulates from the dispensed acetylene gas prior to its discharge from the dispensing assembly.

The dispensing assembly further comprises a coupling 224, for matably engaging the dispensing assembly with downstream piping, valving, or other structure associated with the locus of use of the desorbed acetylene gas, e.g., a burner, spectroscopy installation, chemical synthesis reactor, or microelectronic product manufacturing tool. The acetylene storage and dispensing vessel 204 is shown partially broken away to show the interior monolithic sorbent body 205, which may constitute a carbon pyrolyzate material of the present disclosure, having porosity and physical characteristics as previously described.

The features and advantages of the carbon adsorbent of the present disclosure are more fully shown by the following illustrative embodiments and empirical data.

EXAMPLE

In this example, various carbon adsorbents were evaluated to determine their suitability for acetylene storage and dispensing. These adsorbents included: (1) Kureha bead-shaped activated carbon, having spherical shape, a bulk density of about 0.6 g/mL, a moisture content less than 5%, surface area of 1100-1300 $m^2$ per gram, and an ash content of less than 0.05% (commercially available from Kureha America Inc., New York, N.Y.); (2) Calgon Filtrasorb 600, a bituminous coal based granular activated carbon product (commercially available from Calgon Carbon Corporation, Pittsburgh, Pa.); (3) Maxsorb 19 granular activated carbon having a surface area of 400 to 1000 $m^2$ per gram, a bulk density of approximately 0.55 g per cubic centimeter, and an ash content not exceeding 6% (commercially available from Sai Dhurga Enterprises, Bangalore, Karnataka); (4) Westvaco Nuchar powdered activated carbon (commercially available from Mead Westvaco Corporation, Richmond, Va.), (5) polyvinylidene chloride (PVDC)-based activated carbon pyrolyzate powder (commercially available from ATMI, Inc., Danbury, Conn., USA), and (6) polyvinylidene chloride (PVDC)-based carbon pyrolyzate monolith (commercially available from ATMI, Inc., Danbury, Conn., USA).

In the assessment of these carbon adsorbent materials, carbon dioxide was employed to simulate acetylene, due to the relative ease of handling carbon dioxide and safety issues associated with acetylene, since carbon dioxide has a molecular size that is very close to that of acetylene. BOC Group plc has reported that adsorption isotherms of acetylene and carbon dioxide on a carbonaceous material known as NUXIT-AL are indistinguishable from one another, provided that the data are plotted for the same relative pressure $P/P_0$, wherein $P_0$ is the saturated vapor pressure of the species being absorbed as a liquid phase at temperature T. Since the vapor pressure difference of acetylene and $CO_2$ at room temperature is only about 20%, the acetylene capacity will be on the order of about 90% of the measured $CO_2$ capacity.

The experimental procedure for each of the carbon materials involved determination of adsorption isotherms for the respective materials. A gas supply vessel holding 50 $cm^3$ of gas was employed, as connected to manifold flow circuitry. The system comprising the vessel and manifold flow circuitry was purged with helium gas between pressure of 50 psia (344.7 kPa) and ~$4 \times 10^{-6}$ torr ($5 \times 10^{-4}$ Pa) for five times before leak checking of the system at pressure of about 330 psia (2275.3 kPa). A small heating block was used to degas the 50 $cm^3$ gas supply vessel, involving vacuum baking of the vessel at 180° C. for two hours, to remove moisture impurities from the carbon adsorbent and vessel walls. After degassing, a circulating bath was employed to control the vessel temperature at 21±0.05° C. The carbon dioxide isotherm experiment was carried out according to the following procedure:

Step 1: the 50 cm$^3$ vessel is weighed
Step 2: the carbon adsorbent is weighed and loaded into the vessel
Step 3: the vessel is sealed and its weight measured to confirm sample weight
Step 4: the vessel is connected to the manifold and vacuum is drawn
Step 5: degassing is carried out at 180° C. for two hours under vacuum
Step 6: the vessel is removed from the manifold and weighed
Step 7: the vessel is reloaded and purged with helium for five times
Step 8: the vessel is leak tested with 350 psia (2413.2 kPa) helium
Step 9: the vessel is filled with $CO_2$ at 22 psia (151.7 kPa) pressure for one hour
Step 10: the vessel is sealed and weighed
Step 11: Steps 7 to 10 are repeated with increasing pressure until the pressure in the vessel reaches 250 psia (1723.7 kPa) or the maximum allowed pressure After the isotherm experiment with the vessel loaded with carbon dioxide at maximum pressure, the delivery rates of the $CO_2$ loaded carbon adsorbents were determined by flow through a mass flow controller (MFC) at flow rates of 35 sccm and 70 sccm. Prior to opening the manual valve on the sample vessel, the manifold was evacuated, and manifold pressure was allowed to stabilize for about one hour after the opening of the manual valve. Due to the relative large dead space in the manifold, as compared to the sample vessel, the pre-release pressure was only about half of the vessel pressure. The $CO_2$ delivery rate experiment was carried out according to the following procedure:

Step 1: the manifold is evacuated after leak check/helium purging
Step 2: the vessel manual valve is opened for ~1 hr. of pressure stabilization
Step 3: a manifold valve upstream of the MFC is opened and pressures recorded before and after
Step 4: a manifold valve downstream from the MFC is opened and the MFC is controlled to maintain flow of 100 sccm $N_2$, or 70 sccm for $CO_2$
Step 5: the time elapsed and manifold pressure are measured, until the system pressure reaches about 22 psia (151.7 kPa)
Step 6: the valves opened in Steps 3 and 4 are closed, to allow the system pressure to rise due to residual $CO_2$ inside the sample vessel
Step 7: the sample vessel is removed and weighed
Step 8: the sample vessel is filled with $CO_2$ at maximum pressure after leak checking and helium purging
Step 9: the delivery run is repeated with the MFC set at 50 sccm $N_2$ (~35 sccm $CO_2$)

Figure 2:
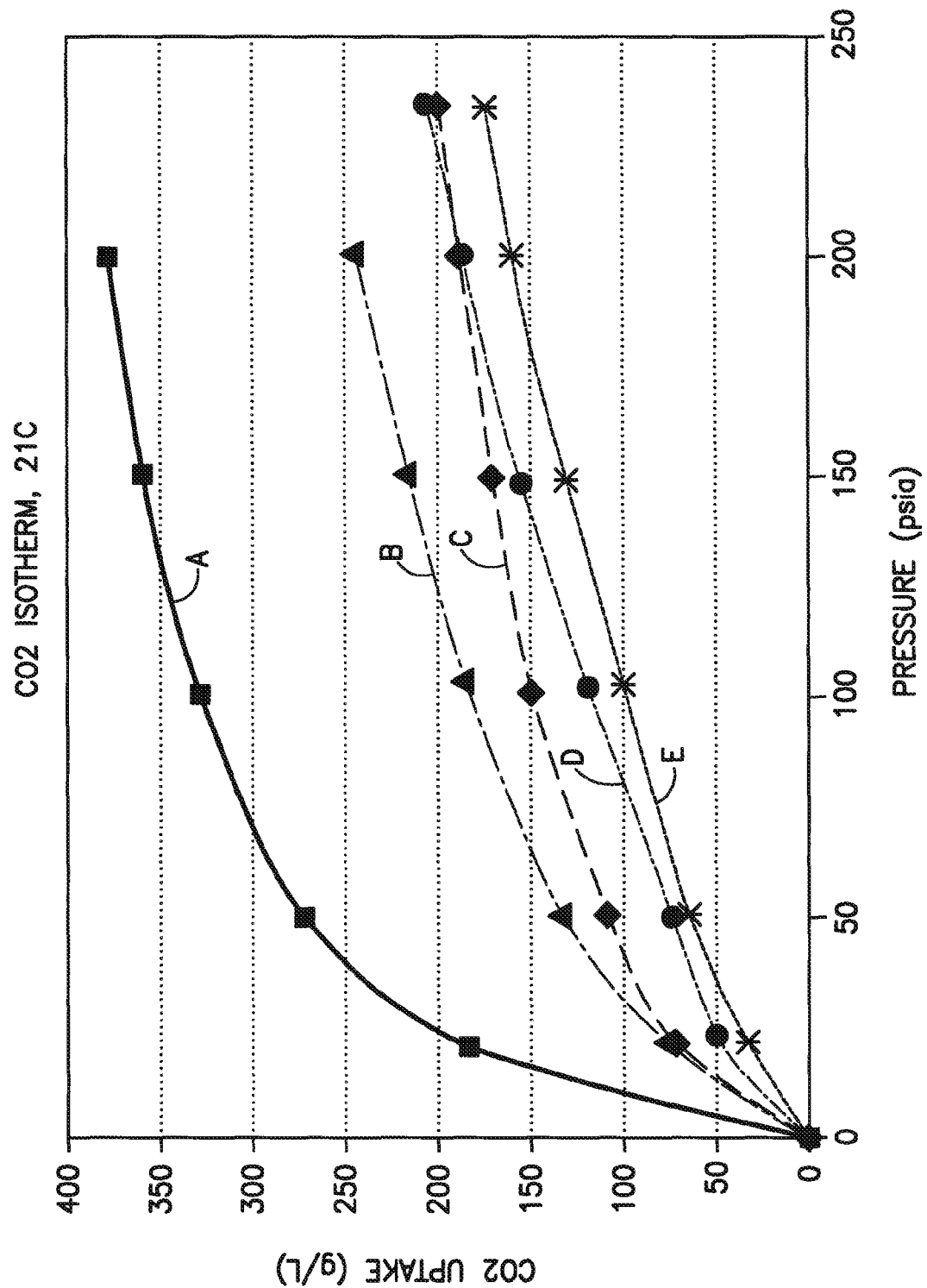
FIG. 2 is a graph of carbon dioxide isotherm results for various carbons based on volume, to simulate their performance when employed to adsorb and desorb acetylene.
Figure 3:
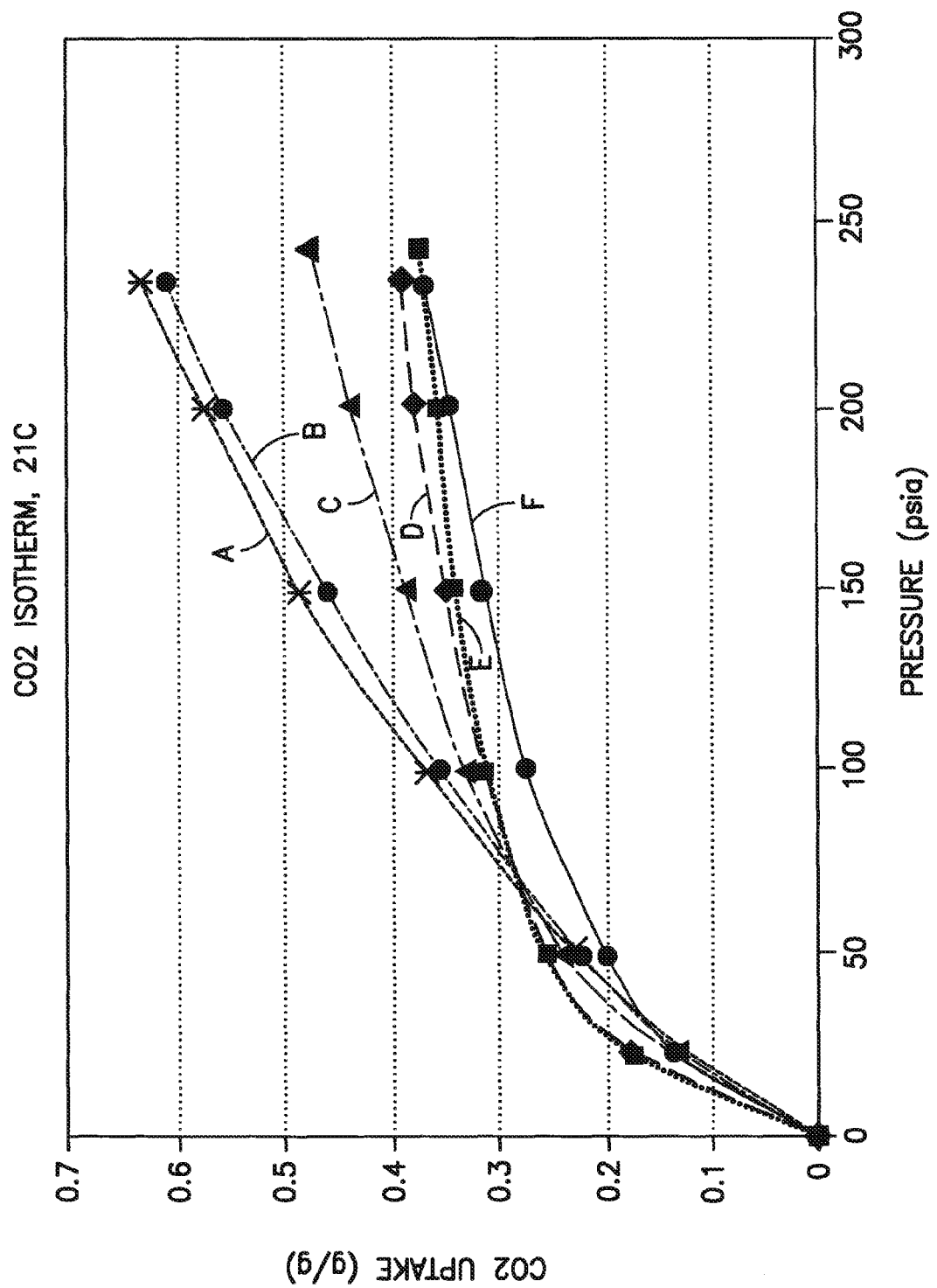
FIG. 3 is a graph of carbon dioxide adsorption capacity of various carbons based on mass, to simulate their performance when employed to store acetylene for subsequent dispensing.

The data from the $CO_2$ isotherm experiment is shown in FIG. 2 and in Table 1 below, as the normalized $CO_2$ adsorption capacity, based on volume, in grams per liter for the various carbons. The data show a close relationship of such normalized $CO_2$ adsorption capacity and the packing density of the adsorbent. The PVDC monolith yielded the highest $CO_2$ uptake during the isotherm test, due to its high density, however its actual usable capacity, defined as the capacity difference between maximum pressure and 22 psia (151.7 kPa), was not much greater than those of the other carbons, since the PVDC monolith also possessed a high adsorption capacity at 22 psia (151.7 kPa).

TABLE 1

| $CO_2$ volume-based capacity (reversible uptake) at 235 psia | | | | | | |
|---|---|---|---|---|---|---|
| Pressure (psia) | Kureha carbon | PVDC monolith | PVDC powder | Calgon F600 | Max-Sorb 19 | West-vaco Nuchar |
| 22 | 77 | 187 | 93 | 75 | 51 | 35 |
| 235 | 265* | 391* | 195 | 200 | 205 | 175 |
| Packing density (g/cc) | 0.56 | 1.06 | 0.5 | 0.55 | 0.32 | 0.29 |
| Capacity (g/L) | 188 | 204 | 102 | 125 | 154 | 140 |

*At 243 psia

Table 2 below shows the mass-based adsorption capacity of the various carbons that were evaluated. When calculated on a mass basis, the PVDC monolith exhibited the lowest capacity, while the low density Maxsorb 19 and Nuchar carbon adsorbents yielded capacities more than twice that of PVDC. Both Maxsorb 19 and Nuchar exhibited a favorable (large slope) isotherm curve and high $CO_2$ uptake at high pressure, and such materials have high surface area (~2000 m$^2$/g).

TABLE 2

| $CO_2$ capacity comparison at 235 psia for various carbons. | | | | | | |
|---|---|---|---|---|---|---|
| | Kureha carbon | PVDC monolith | PVDC powder | Calgon F600 | MaxSorb 19 | Westvaco Nuchar |
| Packing density (g/cc) | 0.56 | 1.06 | 0.5 | 0.55 | 0.32 | 0.29 |
| Capacity (g/L) | 188* | 204* | 102 | 125 | 154 | 140 |
| Capacity (g/g) | 0.337* | 0.193* | 0.205 | 0.23 | 0.509 | 0.486 |

*At 243 psia

One of the main disadvantages of current acetylene storage systems is their inability to provide acetylene at high flow rates. Consequently, delivery rates of $CO_2$ from carbon storage packages were studied, utilizing the various carbon adsorbents described above. The objective of dispensing the $CO_2$ surrogate gas is to verify that the acetylene can be discharged from the absorbent vessel at a sufficient flow rate.

Table 3 below shows the utility rates of the various carbon adsorbents under different release rates. The utility rate is calculated by dividing the amount of $CO_2$ gas delivered from a given adsorbent by the reversible capacity of the adsorbent. When the $CO_2$ stored in the Kureha carbon was released at a flow rate of 3.69 lpm only about 12% of the adsorbed $CO_2$ was utilized. The utility rate improved to 84% when the release rate was dropped to 1.85 lpm. This is equivalent to a delivery rate of ~16 lpm for a small 2B bottle with 2.76 lbs (8.6 liter) capacity.

TABLE 3

Utility rates of various carbon adsorbents.

| Absorbent | Release Rate (lpm/liter adsorbent) | Release Time (min) | Utility Rate (%) |
|---|---|---|---|
| Kureha | 3.69 | ~3 | 12 |
| Kureha | 1.85 | 44 | 84 |
| Kureha | 0.93 | 92 | 88 |
| PVDC monolith | 1.98 | 37 | 70.5 |
| PVDC monolith | 0.99 | 83 | 80 |
| PVDC Powder | 0.87 | 52 | 87 |
| Calgon F600 | 0.87 | 57 | 85 |
| MaxSorb 19 | 1.75 | 38 | 84.4 |
| Westvaco Nuchar | 1.75 | 36 | 88 |

The foregoing data show that both the Kureha carbon and the PVDC pyrolyzed carbon monolith provide sufficient volume-based capacity and release rate for acetylene storage applications, based on the $CO_2$ isotherm and delivery studies.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A carbon adsorbent adapted for adsorptive storage and subsequent desorptive release of decomposition-susceptible gas, said carbon adsorbent comprising porosity in which mesopore volume is less than 0.25 cm$^3$/gm of carbon adsorbent, in which said porosity comprises at least 80% by volume micropores, and at least 65% by volume of said micropores have pore diameter in a range of from 0.3 to 0.72 nm, wherein said carbon adsorbent has a nitrogen adsorption BET surface area greater than 800 m$^2$/g of carbon adsorbent, as measured at 77° K, and a bulk density that is greater than 0.55 g/cc of carbon adsorbent.

2. The carbon adsorbent of claim 1, comprising a pyrolyzate of polyvinylidene chloride.

3. The carbon adsorbent of claim 1, having a fill density measured for acetylene gas at 25° C. and pressure of 650 Torr (86.7 kPa), of greater than 100 g acetylene/liter of carbon adsorbent.

4. The carbon adsorbent of claim 1, having decomposition-susceptible gas adsorbed thereon.

5. The carbon adsorbent of claim 4, wherein said decomposition-susceptible gas comprises gas selected from the group consisting of: formaldehyde; acetylene compounds of the formula $R^1$—C≡C—$R^2$ in which each of $R^1$ and $R^2$ is independently selected from H, $C_1$-$C_{12}$ alkyl, $C_6$-$C_{10}$ aryl, $C_6$-$C_{12}$ cycloalkyl, amino, alkylamino, dialkylamino, alkylaryl wherein alkyl is $C_1$-$C_{12}$ alkyl and aryl is $C_6$-$C_{10}$ aryl, arylalkyl wherein alkyl is $C_1$-$C_{12}$ alkyl and aryl is $C_6$-$C_{10}$ aryl, silyl, and $R^3$Si— wherein each $R^3$ is independently selected from H and $C_1$-$C_{12}$ alkyl; other non-saturated straight chain hydrocarbons; methylene; ethylene; diborane; boranes; germane; fluorogermanes; carboranes; alanes; aluminium hydrides; silane; chlorosilanes; digallane; chlorogallanes; and stannane.

6. The carbon adsorbent of claim 4, wherein said decomposition-susceptible gas comprises acetylene.

7. The carbon adsorbent of claim 1, which has been treated by a treatment that is effective to passivate or deactivate adsorbent surface thereof so that interaction of decomposition-susceptible gas with said surface is restricted to physical adsorption without chemical reaction.

8. The carbon adsorbent of claim 7, wherein said treatment is selected from the group consisting of:
 (i) chemical treatment to remove Lewis acid sites of the adsorbent;
 (ii) surface neutralization treatment;
 (iii) a process comprising: (a) cyclically purging the carbon adsorbent with an inert gas; (b) heating the carbon adsorbent under vacuum to elevated temperature; (c) subsequently cyclically purging the carbon adsorbent with an inert gas; (d) contacting the carbon adsorbent with a low concentration of an intended storage gas at elevated temperature; (e) removing the storage gas; and (f) cooling the carbon adsorbent under vacuum to ambient temperature; and
 (iv) a process comprising: (a) cyclically purging the carbon adsorbent with an inert gas; (b) heating the carbon adsorbent under vacuum to elevated temperature; (c) cooling the carbon adsorbent under vacuum to ambient temperature; (d) gradually contacting the carbon adsorbent with a low concentration of an intended storage gas; (e) warming the vessel containing the gas to a temperature in a range of from 35° C. to 180° C.; (f) allowing the vessel pressure to stabilize; (g) evacuating and cycle purging the carbon adsorbent; and (h) cooling the carbon adsorbent under vacuum to ambient temperature.

9. A decomposition-susceptible gas storage and dispensing package, comprising a gas storage and dispensing vessel comprising an interior volume, and carbon adsorbent of claim 1 disposed in said interior volume.

10. The decomposition-susceptible gas storage and dispensing package of claim 9, further comprising a deflagration suppression component or assembly that is configured to suppress deflagration of decomposition-susceptible gas deriving from the gas storage and dispensing vessel.

11. The decomposition-susceptible gas storage and dispensing package of claim 9, as integrated with a transport vehicle.

12. The decomposition-susceptible gas storage and dispensing package of claim 9, wherein the gas storage and dispensing vessel comprises a tube trailer vessel.

13. The decomposition-susceptible gas storage and dispensing package of claim 9, comprising decomposition-susceptible gas adsorbed on said carbon adsorbent, wherein said decomposition-susceptible gas comprises gas selected from the group consisting of: formaldehyde; acetylene compounds of the formula $R^1$—C≡C—$R^2$ in which each of $R^1$ and $R^2$ is independently selected from H, $C_1$-$C_{12}$ alkyl, $C_6$-$C_{10}$ aryl, $C_6$-$C_{12}$ cycloalkyl, amino, alkylamino, dialkylamino, alkylaryl wherein alkyl is $C_1$-$C_{12}$ alkyl and aryl is $C_6$-$C_{10}$ aryl, arylalkyl wherein alkyl is $C_1$-$C_{12}$ alkyl and aryl is $C_6$-$C_{10}$ aryl, silyl, and $R^3$Si— wherein each $R^3$ is independently selected from H and $C_1$-$C_{12}$ alkyl; other non-saturated straight chain hydrocarbons; methylene; ethylene;

diborane; boranes; germane; fluorogermanes; carboranes; alanes; aluminium hydrides; silane; chlorosilanes; digallane; chlorogallanes; and stannane.

14. The decomposition-susceptible gas storage and dispensing package of claim 13, wherein said decomposition-susceptible gas comprises acetylene.

15. The decomposition-susceptible gas storage and dispensing package of claim 9, wherein the carbon adsorbent has been treated by a treatment that is effective to passivate or deactivate adsorbent surface thereof so that interaction of decomposition-susceptible gas with said surface is restricted to physical adsorption without chemical reaction.

16. The decomposition-susceptible gas storage and dispensing package of claim 15, wherein said treatment is selected from the group consisting of:
  (i) chemical treatment to remove Lewis acid sites of the adsorbent;
  (ii) surface neutralization treatment;
  (iii) a process comprising: (a) cyclically purging the carbon adsorbent with an inert gas; (b) heating the carbon adsorbent under vacuum to elevated temperature; (c) subsequently cyclically purging the carbon adsorbent with an inert gas; (d) contacting the carbon adsorbent with a low concentration of an intended storage gas at elevated temperature; (e) removing the storage gas; and (f) cooling the carbon adsorbent under vacuum to ambient temperature; and
  (iv) a process comprising: (a) cyclically purging the carbon adsorbent with an inert gas; (b) heating the carbon adsorbent under vacuum to elevated temperature; (c) cooling the carbon adsorbent under vacuum to ambient temperature; (d) gradually contacting the carbon adsorbent with a low concentration of an intended storage gas; (e) warming the vessel containing the gas to a temperature in a range of from 35° C. to 180° C.; (f) allowing the vessel pressure to stabilize; (g) evacuating and cycle purging the carbon adsorbent; and (h) cooling the carbon adsorbent under vacuum to ambient temperature.

17. The decomposition-susceptible gas storage and dispensing package of claim 9, coupled in dispensing relationship to a process tool adapted for utilizing said decomposition-susceptible gas.

18. A method of packaging decomposition-susceptible gas for use in supplying same at a point of use, said method comprising adsorbing the decomposition-susceptible gas on a carbon adsorbent according to claim 1, to enable the decomposition-susceptible gas to be provided in absorbed form on said carbon adsorbent at the point of use, for desorption at said point of use, wherein said decomposition-susceptible gas comprises acetylene.

19. The method of claim 18, wherein the carbon adsorbent is provided in a gas storage and dispensing vessel, to which decomposition-susceptible gas is charged for said adsorbing.

20. A method of fabricating a package for use in supply of decomposition-susceptible gas to a point of use thereof, said method comprising fabricating a gas storage and dispensing vessel and disposing therein a carbon adsorbent according to claim 1, wherein said decomposition-susceptible gas comprises acetylene.

21. A method of supplying decomposition-susceptible gas at a point of use, said method comprising providing at said point of use a carbon adsorbent according to claim 1, having the decomposition-susceptible gas adsorbed thereon, and desorbing said decomposition-susceptible gas from said carbon adsorbent at said point of use wherein said decomposition-susceptible gas comprises acetylene.

* * * * *